United States Patent [19]

Baker et al.

[11] Patent Number: 5,693,609

[45] Date of Patent: Dec. 2, 1997

[54] ACYLATED INSULIN ANALOGS

[75] Inventors: Jeffrey C. Baker, Indianapolis; Jose M. Hanquier, Martinsville, both of Ind.

[73] Assignee: Eli Lilly and Company, Indianapolis, Ind.

[21] Appl. No.: 342,931

[22] Filed: Nov. 17, 1994

[51] Int. Cl.$^6$ .......................... A61K 38/28; C07K 14/62
[52] U.S. Cl. ..................... 514/3; 514/4; 514/12; 514/13; 530/303; 530/324; 530/326
[58] Field of Search ..................... 530/326, 324, 530/303; 514/12, 13, 3, 4

[56] References Cited

U.S. PATENT DOCUMENTS

| | | | |
|---|---|---|---|
| 3,823,125 | 7/1974 | Grant et al. | 260/112.7 |
| 3,864,325 | 2/1975 | Smyth | 260/112.7 |
| 3,868,356 | 2/1975 | Smyth | 260/112.7 |
| 3,868,357 | 2/1975 | Smyth et al. | 260/112.7 |
| 3,869,437 | 3/1975 | Lindsay et al. | 260/112.7 |
| 3,950,517 | 4/1976 | Lindsay et al. | 424/178 |

FOREIGN PATENT DOCUMENTS

| | | |
|---|---|---|
| 214826 | 8/1986 | European Pat. Off. |
| 383472 | 2/1990 | European Pat. Off. |
| 1-254699 | 10/1989 | Japan. |
| 1260963 | 1/1972 | United Kingdom. |
| 1415333 | 11/1972 | United Kingdom. |
| 1492997 | 11/1977 | United Kingdom. |
| WO 92/01476 | 2/1992 | WIPO. |
| WO 95/07931 | 3/1995 | WIPO. |
| WO 96/29344 | 9/1996 | WIPO. |

OTHER PUBLICATIONS

Hashimoto, et al, *Pharmaceutical Research*, 6:2, 171–176, (1989).

Scheider, *Journal of Physical Chemistry*, 84:8, 925–928, (1980).

Geiger, et al., *Biological Activity of Insulin Analoques Substituted at the Amino Group of B1–Phenylalanine*, from Proceedings of the Second International Insulin Symposium, Aachen, Germany, Sep. 4–7, 409–415, (1979).

R. Geiger and R. Obermeier, *Contribution of peptide chemistry to our knowledge of insulin and diabetes*, from Proceedings of the Symposium on Proinsulin, Insulin and C–Peptide, Tokushima, 12–14 Jul., 62–72, (1978).

Rösen, et al, *A1–Modified Insulins: Receptor Binding and Biological Activity*, from Proceedings of the Second International Insulin Symposium, Aachen, Germany, Sep. 4–7, 403–408, (1979).

D.G. Lindsay and S. Shall, *Biochem.J.*, 115, 587–595, (1969).

Muranishi, et al., *Journal of Controlled Release*, 19, 179–188, (1992).

Hashizume, et al., *J. Pharm. Pharmacol.*, 44 555–559, (1992).

D.L. Lindsay and S. Shall, *Biochem.J.*, 121, 737–745, (1971).

Lapidot, et al., *Journal of Lipid Research*, 8, 142–145, (1967).

Asada, et al., *Pharmaceutical Research*, 11:8, 1115–1120, (1994).

Inoue, et al., *Biochemistry*, 28:16, 6619–6624, (1989).

Kunitomo, et al., *The Journal of Biological Chemistry*, 267:13, 8732–8738, (1992).

Brem et al. (1992) Protien Engineering vol. 5 No. 6 pp. 527–533.

Carey, Francis A. (1987) Organic Chemistry. McGraw–Hill Book Company pp. 1110–1113.

*Primary Examiner*—Cecilia J. Tsang
*Assistant Examiner*—Anish Gupta
*Attorney, Agent, or Firm*—Steven P. Caltrider; David E. Boone

[57] ABSTRACT

The present invention relates to the field of diabetes. More particularly, the invention relates to a monomeric insulin analog wherein the A chain is the naturally occurring sequence of the human insulin A chain and the B chain is modified at either position B28 and B29 or both. The analog is mono-acylated at the N-terminal of the A chain or B chain or at the lysine. The acylated insulin analogs have an extended duration of action.

33 Claims, No Drawings

SEQUENCE LISTING ( 1 ) GENERAL INFORMATION:

( i i i ) NUMBER OF SEQUENCES:2

( 2 ) INFORMATION FOR SEQ ID NO:1:

( i ) SEQUENCE CHARACTERISTICS:
        ( A ) LENGTH:21 amino acids
        ( B ) TYPE:amino acid
        ( D ) TOPOLOGY:linear ( i i ) MOLECULE TYPE:polypeptide ( i x ) FEATURE:
        ( A ) NAME/KEY:Variable Site
        ( B ) LOCATION:1
        ( C ) IDENTIFICATION METHOD:
        ( D ) OTHER INFORMATION:"Xaa at position 1 of SEQ ID NO:1 is
            Gly; or acylated Gly when Xaa at position 1 of SEQ ID
            NO:2 is Phe, Xaa at position 28 of SEQ ID NO:2 is Asp,
            Lys, Leu, Val, or Ala, and Xaa at position 29 of SEQ.
            ID NO:2 is Lys or Pro."

( x i ) SEQUENCE DESCRIPTION: SEQ ID NO:1:

```
Xaa  Ile  Val  Glu  Gln  Cys  Cys  Thr  Ser  Ile  Cys  Ser  Leu  Tyr  Gln  Leu
 1              5                        10                       15
Glu  Asn  Tyr  Cys  Asn
              20
```

( 2 ) INFORMATION FOR SEQ ID NO:2 :

( i ) SEQUENCE CHARACTERISTICS:
        ( A ) LENGTH:30 amino acids
        ( B ) TYPE:amino acid
        ( D ) TOPOLOGY:linear ( i i ) MOLECULE TYPE:polypeptide ( i x ) FEATURE:
        ( A ) NAME/KEY:Variable Site
        ( B ) LOCATION:1
        ( C ) IDENTIFICATION METHOD:
        ( D ) OTHER INFORMATION:"Xaa at position 1 of SEQ ID NO:2 is
            Phe; or acylated Phe when Xaa at position 1 of SEQ ID
            NO:1 is Gly, Xaa at position 28 of SEQ ID NO:2 is Asp,
            Lys, Leu, Val, or Ala, and Xaa at position 29 of SEQ.
            ID NO:2 is Lys or Pro."

( i x ) FEATURE:
        ( A ) NAME/KEY:Variable Site
        ( B ) LOCATION:28
        ( C ) IDENTIFICATION METHOD:
        ( D ) OTHER INFORMATION:"Xaa at position 28 of SEQ ID NO:2 is
            Asp, Lys, Leu, Val, Ala; or acylated Lys when Xaa at
            position 1 of SEQ ID NO:1 is Gly, Xaa at position 1 of
            SEQ ID NO:2 is Phe, and Xaa at position 29 of SEQ. ID
            NO:2 is Pro."

( i x ) FEATURE:
        ( A ) NAME/KEY:Variable Site
        ( B ) LOCATION:29
        ( C ) IDENTIFICATION METHOD:
        ( D ) OTHER INFORMATION:"Xaa at position 29 of SEQ ID NO:2 is
            Lys, Pro; or acylated Lys when Xaa at position 28 of
            SEQ ID NO:2 is Asp, Lys, Leu, Val, or Ala, Xaa at
            position 1 of SEQ ID NO:1 is Gly, and Xaa at position 1
            of SEQ. ID NO:2 is Phe."

( x i ) SEQUENCE DESCRIPTION: SEQ ID NO:2:

```
Xaa  Val  Asn  Gln  His  Leu  Cys  Gly  Ser  His  Leu  Val  Glu  Ala  Leu  Tyr
 1              5                        10                       15
```

-continued

```
Leu  Val  Cys  Gly  Glu  Arg  Gly  Phe  Phe  Tyr  Thr  Xaa  Xaa  Thr
              20                      25                      30
```

ACYLATED INSULIN ANALOGS

FIELD OF THE INVENTION

The present invention relates to the field of diabetes. More particularly, the invention relates to acylated insulin analogs with an extended duration of action.

BACKGROUND OF THE INVENTION

The availability of insulin replacement therapy has prevented the mortality and morbidity of acute complications in diabetes mellitus. However, chronic diabetic complications remain a major health problem due to persistent metabolic derangement, arising principally from poor control of blood glucose. Results emerging from the Diabetes Control and Complications Trial (DCCT) indicate that a decrease of 1% in Hb Alc correlates with more than 35% improvement in the incidence of retinopathy.

In order to achieve normal glycemia, therapy must be designed to parallel as closely as possible the pattern of endogenous insulin secretion in normal individuals. The daily physiological demand for insulin fluctuates and can be separated into two phases: (a) the absorptive phase requiring a pulse of insulin to dispose of the meal-related blood glucose surge, and (b) the post-absorptive phase requiring a sustained amount of insulin to regulate hepatic glucose output for maintaining optimal fasting blood glucose. Accordingly, effective therapy involves the combined use of two types of exogenous insulin: a fast-acting meal time insulin and a long-acting basal insulin.

To achieve a long-acting basal time action, insulin is currently formulated under conditions favoring formation of a hexamer conformation in an insoluble, crystalline state. These long acting formulations are Ultralente, Lente, and semi-Lente. However, the insolubility of the current long-acting preparations has been shown to cause problems relating to inconsistency in the dose-response as well as unpredictability in time action. In addition, one of the currently available long-acting insulin preparations, beef Ultralente, is immunogenic. The presence of antibodies that results from the immunogenicity of beef Ultralente alters the pharmacokinetics of fast-acting insulins.

While the time action of the insoluble Ultralente formulation makes a convenient once-a-day basal insulin, many physicians actually prefer to use an intermediate time action insulin, an insulin-protamine formulation commonly referred to as insulin-NPH. Insulin-NPH is used twice daily as a basal insulin because it is comparatively easier to adjust the optimal dosage with a drug of shorter time action. As a result, intermediate-acting insulins account for 70% of the U.S., 64% of the Japanese, 45% of European and an overall 55% of the world-wide insulin market.

However, both insoluble insulin-NPH and insoluble Ultralente insulin are suspension formulations. Thus, the formulations are inherently less predictable than soluble formulations and result in less than adequate control of blood glucose and a greater susceptibility to life-threatening hypoglycemic episodes. Accordingly, there remains a need for a soluble, long-acting basal insulin in order to achieve successful intensive insulin replacement therapy. The present invention provides acylated insulin analogs that may be formulated to provide soluble, basal insulin therapy.

The acylation of pork, beef, or human insulin is disclosed by Muranishi and Kiso, in Japanese Patent Application 1-254,699. The following compounds are specifically disclosed: B29-$N^\epsilon$-palmitoyl insulin (the $\epsilon$-amino group is acylated), B1-$N^\alpha$-palmitoyl insulin (the N terminal $\alpha$-amino group of the B chain is acylated), and B1,B29-$N^\alpha N^\epsilon$-dipalmitoyl insulin (both the $\epsilon$-amino and the N-terminal $\alpha$-amino group are acylated). Muranishi and Kiso disclose that acylated insulin possesses a biological profile similar to insulin; but fails to provide the dosages, routes of administration, or other conditions of the in vivo model to allow one skilled in the art to evaluate the activity or duration of action of the acylated insulin.

Similarly, Hashimoto et al., in *Pharmaceutical Research* 6: 171-176 (1989), disclose B1-$N^\alpha$-palmitoyl insulin (the N terminal $\alpha$-amino group is acylated), and B1,B29-$N^\alpha N^\epsilon$-dipalmitoyl insulin (both the $\alpha$-amino and the N-terminal $\alpha$-amino groups are acylated). Hashimoto et al. studied the hypoglycemic effect of B1-$N^\alpha$-palmitoyl insulin and B1,B29-$N\alpha$, $N^\epsilon$-dipalmitoyl insulin in male rats at 25 U/mL, an exceedingly high dose. At these doses, FIG. 5 demonstrates very low activity when administered intravenously. When administered intramuscularly, only a short hypoglycemic effect of B1-$N^\alpha$-palmitoyl insulin and negligible effect of B1,B29-$N^\alpha$, $N^\epsilon$-dipalmitoyl insulin were disclosed in FIG. 6.

In addition to the in vivo reports by Muranishi and Kiso and Hashimoto et al., Walder et al., in PCT publication WO 92/01476, disclose that the half-life of proteins and peptides can be extended in vivo by chemically linking the protein with an apolar group, specifically a fatty acid derivative. The fatty acid provides a bridging group between the protein and albumin. Walder et al. continue to disclose that the apolar group is preferably restricted to a unique site or sites in the protein and exemplify the binding of the cysteine residues of hemoglobin. The reference generally discloses fatty acid derivatives of insulin. However, no fatty acid derivatives of insulin are specifically disclosed or exemplified, and no data are disclosed to indicate that the biological activity of the fatty acid derivatives of insulin is retained.

It has been discovered that the selective acylation of a free amino group of a monomeric insulin analog provides effective basal insulin activity. The unacylated insulin analogs described herein are designed to provide a rapid onset of action and a rapid clearance. These analogs are known in the art as monomeric insulin analogs. The ability to modify such analogs to provide basal activity is most unexpected.

The present invention provides a mono-acylated insulin analog that yields upon use an extended duration of action. The analogs may be prepared in soluble formulations thus offering advantages over current basal insulin therapy. The present analogs also possess excellent predictability in dose response, excellent predictability in time action, lack a distinct peak in the time-action profile, and are ideally suited for the preparation of mixture formulations comprising an insulin analog and acylated insulin analog.

SUMMARY OF THE INVENTION

The present invention provides a mono-acylated insulin analog of the Formula:

| SEQ ID NO:1 | | | | | | | | | | | | | | | |
|---|---|---|---|---|---|---|---|---|---|---|---|---|---|---|---|
| Xaa 1 | Ile | Val | Glu | Gln 5 | Cys | Cys | Thr | Ser | Ile 10 | Cys | Ser | Leu | Tyr | Gln 15 | Leu |
| Glu | Asn | Tyr | Cys 20 | Asn | | | | | | | | | | | | properly cross-linked to SEQ ID NO:2

| Xaa 1 | Val | Asn | Gln | His 5 | Leu | Cys | Gly | Ser | His 10 | Leu | Val | Glu | Ala | Leu 15 | Tyr |
|---|---|---|---|---|---|---|---|---|---|---|---|---|---|---|---|
| Leu | Val | Cys | Gly 20 | Glu | Arg | Gly | Phe | Phe 25 | Tyr | Thr | Xaa | Xaa | Thr 30 | | | or a pharmaceutically acceptable salt thereof;
wherein:

Xaa at position 1 of SEQ ID NO:1 (insulin A-chain) is Gly; or acylated Gly when Xaa at position 1 of SEQ ID NO:2 is Phe, Xaa at position 28 of SEQ ID NO:2 is Asp, Lys, Leu, Val, or Ala, and Xaa at position 29 of SEQ ID NO:2 is Lys or Pro;

Xaa at position 1 of SEQ ID NO:2 (insulin B-chain) is Phe; or acylated Phe when Xaa at position 1 of SEQ ID NO:1 is Gly, Xaa at position 28 of SEQ ID NO:2 is Asp, Lys, Leu, Val, or Ala, and Xaa at position 29 of SEQ ID NO:2 is Lys or Pro;

Xaa at position 28 of SEQ ID NO:2 is Asp, Lys, Leu, Val, Ala; or acylated Lys when Xaa at position 1 of SEQ ID NO:1 is Gly, Xaa at position 1 of SEQ ID NO:2 is Phe, and Xaa at position 29 of SEQ ID NO:2 is Pro; and Xaa at position 29 of SEQ ID NO:2 is Lys, Pro; or acylated Lys when Xaa at position 28 of SEQ ID NO:2 is Asp, Lys, Leu, Val, or Ala, Xaa at position 1 of SEQ ID NO:1 is Gly, and Xaa at position 1 of SEQ ID NO:2 is Phe.

The invention further provides a method of treating hyperglycemia by administering to a patient in need thereof a pharmaceutical composition containing an effective amount of an acylated insulin analog of the invention in combination with one or more pharmaceutically acceptable excipients.

Also disclosed and claimed are parenteral pharmaceutical formulations, which comprise an acylated insulin analog of the present invention together with one or more pharmaceutically acceptable preservatives, isotonicity agents, or buffers.

DETAILED DESCRIPTION

All amino acid abbreviations used in this disclosure are those accepted by the United States Patent and Trademark Office as set forth in 37 C.F.R. § 1,822(B)(2).

The term "cross-link" means the formation of disulfide bonds between cysteine residues. A properly cross-linked human insulin or insulin analog contains three disulfide bridges. The first disulfide bridge is formed between the cysteine residues at positions 6 and 11 of the A-chain. The second disulfide bridge links the cysteine residues at position 7 of the A-chain to the cysteine at position 7 of the B-chain. The third disulfide bridge links the cysteine at position 20 of the A-chain to the cysteine at position 19 of the B-chain.

The terms "acylated. Gly," "acylated Phe," and "acylated Lys" refer to Gly, Phe, or Lys acylated with a $C_6$–$C_{21}$ fatty acid. The term "acylating group" refers to the fatty acid chemically bonded to the α-amino group or ε-amino group of the insulin analog. The free amino groups at positions A1 and B1 are α-amino groups. The free amino group of Lys at position B28 or B29 is an ε-amino group.

The term "acylating" means the introduction of one acyl groups covantly bonded to a free amino group of the protein. The term "selective acylation" means the preferential acylation of the ε-amino group(s) over the α-amino groups.

The term "fatty acid" means a saturated or unsaturated $C_6$–$C_{21}$ fatty acid. The preferred fatty acids are saturated and include myristic acid ($C_{14}$), pentadecylic acid ($C_{15}$), palmitic acid ($C_{16}$), heptadecylic acid ($C_{17}$) and stearic acid ($C_{18}$). Most preferably, the fatty acid is palmitic acid. The compounds of the present invention represent mono-acylated insulin analogs. The insulin analogs are acylated at an α-amino group or ε-amino group with a $C_6$–$C_{21}$ fatty acid. Preferably, the analogs are mono-acylated at the ε-amino group of lysine.

The term "activated fatty acid ester" means a fatty acid which has been activated using general techniques described in Methods of Enzymology, 25, 494–499 (1972) and Lapidot et al., in J. of Lipid Res. 8: 142–145 (1967). Activated fatty acid ester includes derivatives of commonly employed acylating agents such as hydroxybenzotriazide (HOBT), N-hydroxysuccinimide and derivatives thereof. The preferred activated ester is N-succinimidyl palmitate.

The term "soluble" indicates that a sufficient amount of ester is present in the liquid phase to acylate the insulin analog. Preferably, 1 to 2 molar equivalents of activated ester per mole of analog are in the liquid phase.

The term "monomeric insulin analog" or "insulin analog" as used herein is a fast-acting insulin analog that is less prone to dimerization or self-association. Monomeric insulin analog is human insulin wherein Pro at position B28 is substituted with Asp, Lys, Leu, Val, or Ala, and Lys at position B29 is Lysine or Proline. Monomeric insulin analogs are described in Chance et al., U.S. patent application Ser. No. 07/388,201, (EPO publication number 383 472), and Brange et al., EPO publication 214 826. One skilled in the art would recognize that other modifications to the monomeric insulin analog are possible and widely accepted in the art. These modifications include replacement of the Histidine residue at position B10 with Aspartic acid; replacement of the Phenylalanine residue at position B1 with Aspartic acid; replacement of the Threonine residue at position B30 with Alanine; replacement of the Serine residue at position B9 with Aspartic acid; deletion of amino acids at position B1 alone or in combination with a deletion at position B2; and deletion of Threonine from position B30.

The term "basic conditions" as used herein refers to the basicity of the reaction. To selectively acylate an insulin analog at the ε-amino group, the reaction must be carried out with substantially all the free amino groups deprotonated. In an aqueous solvent or co-solvent, basic conditions means the reaction is carried out at a pH greater than 9.0. In an organic solvent, the reaction is carried out in the presence of a base with basicity equivalent to a $pK_a$ greater than or equal to 10.75 in water.

SEQ ID NO: 1 refers to the first sequence set forth in the sequence listing and means an analog of the human insulin A-chain with the sequence:

| Xaa 1 | Ile | Val | Glu | Gln 5 | Cys | Cys | Thr | Ser | Ile 10 | Cys | Ser | Leu | Tyr | Gln 15 | Leu |
|---|---|---|---|---|---|---|---|---|---|---|---|---|---|---|---|
| Glu | Asn | Tyr | Cys 20 | Asn | | | | | | | | | | | | wherein Xaa at position 1 of SEQ ID NO:1 (insulin A-chain) is Gly; or acylated Gly when Xaa at position 1 of SEQ ID NO:2 is Phe, Xaa at position 28 of SEQ ID NO:2 is Asp, Lys, Leu, Val, or Ala, and Xaa at position 29 of SEQ ID NO:2 is Lys or Pro.

SEQ ID NO: 2 refers to the second sequence set forth in the sequence listing and means an analog of the human insulin B-chain with the sequence:

| Xaa 1 | Val | Asn | Gln | His 5 | Leu | Cys | Gly | Ser | His 10 | Leu | Val | Glu | Ala | Leu 15 | Tyr |
|---|---|---|---|---|---|---|---|---|---|---|---|---|---|---|---|
| Leu | Val | Cys | Gly 20 | Glu | Arg | Gly | Phe | Phe 25 | Tyr | Thr | Xaa | Xaa | Thr 30 | | | wherein:
  Xaa at position 1 of SEQ ID NO:2 (insulin B-chain) is Phe; or acylated Phe when Xaa at position 1 of SEQ ID NO:1 is Gly, Xaa at position 28 of SEQ ID NO:2 is Asp, Lys, Leu, Val, or Ala, and Xaa at position 29 of SEQ ID NO:2 is Lys or Pro;
  Xaa at position 28 of SEQ ID NO:2 is Asp, Lys, Leu, Val, Ala; or acylated Lys when Xaa at position 1 of SEQ ID NO:1 (insulin A-chain) is Gly, Xaa at position 1 of SEQ ID NO:2 (insulin B-chain) is Phe, and Xaa at position 29 of SEQ ID NO:2 is Pro; and
  Xaa at position 29 of SEQ ID NO:2 is Lys, Pro; or acylated Lys when Xaa at position 28 of SEQ ID NO:2 is Asp, Lys, Leu, Val, or Ala, Xaa at position 1 of SEQ ID NO:1 (insulin A-chain) is Gly, and Xaa at position 1 of SEQ ID NO:2 (insulin B-chain) is Phe.

As noted above, the present invention provides a monoacylated insulin analog of the formula: SEQ ID NO:1 properly cross-linked to SEQ ID NO:2, or a pharmaceutically acceptable salt thereof. The preferred amino acid residue at position 1 of SEQ ID NO:1 (insulin A-chain) is Gly. Phenylalanine is the preferred amino acid at position 1 of SEQ ID NO:2 (insulin B-chain). The preferred amino acid residue at position 28 of SEQ ID NO:2 is Asp; or acylated Lys when the amino acid residue at position 29 of SEQ ID NO:2 is Pro. The preferred amino acid residue at position 29 of SEQ ID NO:2 is Lys; or Pro when the amino acid residue at position 28 of SEQ ID NO:2 is acylated Lys. In standard-biochemical terms known to the skilled artisan, the preferred analog is mono-acylated $Lys^{B28}Pro^{B29}$-human insulin. Most preferred acylated insulin analogs are mono-acylated with a $C_{14}$ to $C_{18}$ fatty acid and include B29-$N^\epsilon$-$Asp^{B28}$-palmitoyl human insulin ($B^{28}$ is Asp; $B^{29}$ is acylated Lys) and B28-$N^\epsilon$-palmitoyl-$Lys^{B28}Pro^{B29}$-human insulin ($B^{28}$ is acylated Lys; $B^{29}$ is Pro).

The acylation of free amino groups of proteins, including insulin, is known in the art. General methods of acylation are set forth in *Methods of Enzymology*, 25: 494–499 (1972) and include the use of activated esters, acid halides, or acid anhydrides. The use of activated esters, in particular N-hydroxysuccinimide esters, of fatty acids is a particularly advantageous means of acylating a free amino acid with a fatty acid. Lapidot et al., *J. of Lipid Res.* 8: 142–145 (1967). Lapidot et al. describe the preparation of N-hydroxysuccinimide esters and their use in the preparation of N-lauroyl-glycine, N-lauroyl-n-serine, and N-lauroyl-L-glutamic acid.

To selectively acylate the ε-amino group, various protecting groups may be used to block the α-amino group during the coupling. The selection of a suitable protecting group is known to one skilled in the art and includes p-methoxybenzoxycarbonyl (pmZ). Preferably, the ε-amino group is acylated in a one step synthesis without the use of amino-protecting groups. The acylation is carried out by reacting the activated fatty acid ester with the ε-amino group of the protein under basic conditions in a polar solvent. The basicity of the reaction must be sufficient to deprotonate all the free amino groups of the insulin analog. Under weakly basic conditions, all the free amino groups are not deprotonated and preferential acylation of the N-terminal or α-amino groups results. In an aqueous solvent or co-solvent, basic conditions means the reaction is carried out at a pH greater than 9.0. Because protein degradation results at a pH range exceeding 12.0, the pH of the reaction mixture is preferably 10.0 to 11.5, and most preferably 10.5. The pH measurement of the reaction of the reaction mixture in a mixed organic and aqueous solvent is the pH of the aqueous solvent prior to mixing.

In a non-aqueous solvent, the selective acylation of the ε-amino group is carried out in the presence of a base with basicity equivalent to a $pK_a$ greater than or equal to 10.75 in water in order to sufficiently deprotonate the ε-amino group (s). That is, the base must be at least as strong as triethylamine. Preferably, the base is tetramethylguanidine, diisopropylethylamine, or tetrabutylammonium hydroxide. The use of a weaker base results in the acylation of the α-amino groups.

The choice of solvent is not critical and dependent largely on the solubility of the insulin analog and the fatty acid ester. The solvent may be wholly organic. Generally acceptable organic solvents include DMSO, DMF and the like. Aqueous solvent and mixtures of aqueous and organic solvents are also operable. The selection Of the polar solvents is limited only by the solubility of the reagents. Preferred solvents are DMSO; DMF; acetonitrile and water; acetone and water; ethanol and water; isopropyl alcohol and water; isopropyl alcohol, ethanol, and water; and ethanol, propanol and water. Preferably, the solvent is acetonitrile and water;

most preferably 50% acetonitrile. One skilled in the art would recognize that other polar solvents are also operable.

Generally, it is preferred that the activated fatty acid ester be in molar excess. Preferably the reaction is carried out with 1 to 4 molar equivalents, most preferably 1 to 2 molar equivalents, of the ester. One skilled in the art would recognize that at very high levels of activated ester, bis- or tri-acylated product will be produced in significant quantity.

The temperature of the reaction is not critical. The reaction is carried out at between 20 to 40 degrees Celsius and is generally complete in 15 minutes to 24 hours.

After acylation, the product is purified by standard methods such as reverse phase or hydrophobic chromatography. Thereafter, the product is recovered by standard methods such freeze drying or by crystallization.

The monomeric insulin analogs of the present invention can be prepared by any of a variety of recognized peptide synthesis techniques including classical (solution) methods, solid phase methods, semi-synthetic methods, and more recent recombinant DNA methods. For example, Chance et al., U.S. patent application Ser. No. 07/388,201, EPO publication number 383 472, and Brange et al., EPO 214 826, disclose the preparation of various insulin analogs and are herein incorporated by reference. The A and B chains of the insulin analogs of the present invention may also be prepared via a proinsulin-like precursor molecule using recombinant DNA techniques. See Frank et al., *Peptides: Synthesis-Structure-Function* Proc. Seventh Am. Pept. Symp., Eds. D. Rich and E. Gross (1981) which is incorporated herein by reference.

The following example is provided merely to further illustrate the invention. The scope of the invention is not construed as merely consisting of the following example.

EXAMPLE 1

Acylation of $Lys^{B28}$ $Pro^{B29}$-Human Insulin Using N-Succinimidyl Palmitate in Acetonitrile and Water $Lys^{B28}Pro^{B29}$-human insulin crystals (2.22 g) were dissolved in 100 mL of 50 mM boric acid solution at pH 2.5. The pH of the solution was readjusted to 2.5 using 10% HCl, and the solution was stirred until the crystals were fully dissolved by visual inspection. A solution of activated ester (N-Succinimidyl Palmitate) was prepared by adding 270 mg of the solid activated ester to 27 mL of acetonitrile preheated to approximately 50° C., and vigorously stirring until all the activated ester particles were in solution by visual inspection. The pH of the solution was adjusted to approximately 10.22 by the addition of 10% NaOH, and the solution was allowed to stir at 4° C. for 15 minutes. Acetonitrile (73 mL) was added to the pH adjusted solution, followed by the previously prepared activated ester solution. The reaction was allowed to proceed at 4° C. for 85 minutes, and was quenched by adding 1N acetic acid (600 mL), resulting in a pH of 2.85. The reaction yield calculated as the amount of B28-N$^\epsilon$-Palmitoyl $Lys^{B28}Pro^{B29}$-human insulin in the quenched reaction divided by the initial amount of $Lys^{B28}Pro^{B29}$-human insulin was 72.5%.

As noted previously, the acylated insulin analogs of the present invention are effective in treating hyperglycemia by administering to a patient in need thereof an effective amount of a mono-acylated insulin analog. As used herein the term "effective amount" refers to that amount of one or more acylated analogs of the present invention needed to lower or maintain blood sugar levels either therapeutically or prophylactically. This amount typically may range from about 10 units or more per day (or about 0.3 to about 2 mg assuming approximately 29 units per mg). However, it is to be understood that the amount of the acylated analog(s) actually administered will be determined by a physician in light of the relevant circumstances including the condition being treated (i.e. the cause of the hyperglycemia) the particular analog to be administered, the chosen parenteral route of administration, the age, weight and response of the individual patient and the severity of the patient's symptoms. Therefore, the above dosage ranges are not intended to limit the scope of the invention in any manner.

The acylated insulin analogs of the invention are administered to a patient in need thereof (i.e. a patient suffering from hyperglycemia) by means of pharmaceutical compositions containing an effective amount of at least one mono-acylated insulin analog in combination with one or more pharmaceutically acceptable excipients or carriers. For these purposes, the pharmaceutical compositions may typically be formulated so as to contain about 100 units per mL or similar concentrations containing an effective amount of the acylated insulin analog(s). These compositions are typically, though not necessarily, parenteral in nature and may be prepared by any of a variety of techniques using conventional excipients or carriers for parenteral products which are well known in the art. See, for example, *Remington's Pharmaceutical Sciences* 17th Edition, Mack Publishing Company, Easton, Pa., U.S.A. (1985) which is incorporated herein by reference. For example, dosage forms for parenteral administration may be prepared by suspending or dissolving the desired amount of at least one mono-acylated insulin analog in a non-toxic liquid vehicle suitable for injection such as an aqueous medium and sterilizing the suspension or solution. Alternatively, a measured amount of the compound may be placed in a vial; and the vial and its contents sterilized and sealed. An accompanying vial or vehicle can be provided for purposes of mixing prior to administration.

Pharmaceutical compositions adapted for parenteral administration employ diluents, excipients and carriers such as water and water-miscible organic solvents such as glycerin, sesame oil, groundnut oil, aqueous propylene glycol, N,N-dimethylformamide and the like. Examples of such pharmaceutical compositions include sterile, isotonic, aqueous saline solutions of the mono-acylated insulin analog that can be buffered with a pharmaceutically acceptable buffer and that are pyrogen free. Additionally, the parenteral pharmaceutical formulation may contain preservatives such as meta-cresol or other agents to adjust pH of the final product such as sodium hydroxide or hydrochloric acid.

The acylated insulin analogs of the present invention may also be formulated as mixtures. The mixture formulations comprise unacylated insulin or insulin analog, and an acylated insulin analog. The ratio of the insulin or insulin analog to acylated analog is from 1:99 to 99:1 on a weight basis. Preferably, the ratio is from 75:25 to 25:75; most preferably from 40:60 to 60:40; and still most preferably, 50:50. The mixture formulations are prepared by mixing the desired volumes of the components in a standard parenteral formulation diluent. Standard diluents include an isotonicity agent, zinc, a physiologically tolerated buffer and a preservative. The physiologically tolerated buffer is preferably a phosphate buffer, like dibasic sodium phosphate. Other physiologically tolerated buffers include TRIS or sodium acetate. The selection and concentration of buffer is known in the art. Pharmaceutically acceptable preservatives include phenol, m-cresol, resorcinol, and methyl paraben. The mixture formulations of the present invention are particularly advantageous because both the relatively fast-acting insulin or insulin analog and the mono-acylated insulin analog are soluble in the formulation. Thus, providing a predictable duration of action profile.

The following formulation example is illustrative only and not intended to limit the scope of the invention in any way.

FORMULATION 1

An parenteral formulation may be prepared as follows:

|  | Quantity |
| --- | --- |
| Phenol | 30 mM |
| Glycerin | 16 mg/mL |
| Acylated Lys$^{B28}$Pro$^{B29}$-human insulin | 100 U |
| Zinc | 0.7% |
| Sodium acetate | 3.8 mg/mL |

The solution of the above ingredients is administered by injection to a subject in need of treatment.

To demonstrate the efficacy of the compounds of the present invention, B28-N$^{\epsilon}$-Palmitoyl Lys$^{B28}$Pro$^{B29}$-human insulin was tested in a conscious dog model. Experiments were conducted in overnight-fasted, conscious, adult (1–2 years of age) male and female beagles weighing 8–15 kg. At least ten days prior to the study, animals were anesthetized with isoflurane, and a cut-down was made in the left or right inguinal region. Silastic catheters were inserted into the femoral artery and into the proximal caudal femoral vein and secured with 4-0 silk suture. The free ends of the catheters were passed subcutaneously to the back using a trocar needle. The catheters were then filled with a glycerol/heparin solution (3:1, v/v; final heparin concentration of 250 KIU/ml), and the free ends were knotted and placed in a subcutaneous pocket to allow complete closure of the skin. Keflex was administered both pre-operatively (20 mg/kg, IV and 20 mg/kg, I.M.) and post-operatively (250 mg, p.o. once daily for seven days) to prevent infections. Torbugesic (1.5 mg/kg, I.M.) was administered post-operatively to control pain. Blood was drawn just prior to the study day to determine the health of the animal. Only animals with hematocrits above 38% and leukocyte counts below 16,000/mm$^3$ were used. The afternoon before the experiment, the free ends of the catheters were exteriorized from the subcutaneous pocket through a small incision made under local anesthesia (2% lidocaine), and the dog was fitted with a tether system jacket and collar assembly. The morning of the experiment, the contents of the arterial catheter were aspirated (only the arterial line was used in these studies), the catheter was flushed with saline, and an extension line (protected by a stainless steel tether) was attached to the catheter. The dog was placed in a metabolic cage, and the catheter extension line and tether was attached to a swivel system to allow the dog to move freely about the cage. After a 15 minute rest period (45 minutes, controls), blood (2–3.5 ml) was drawn for determination of the plasma glucose concentration. A second baseline sample was drawn 15 minutes later (0 time). Test substance (phosphate buffered saline or 10.5 mmoles/kg of B28-N$^{\epsilon}$-Palmitoyl Lys$^{B28}$Pro$^{B29}$-human insulin; this does is the molar equivalent of 1.75 U/kg of human insulin) was administered subcutaneously in the dorsal of the neck.

Arterial blood samples (2–3.5 ml) were then taken at least every 30 minutes for the next two (controls) to six (B28-N$^{\epsilon}$-palmitoyl Lys$^{B28}$Pro$^{B29}$-human insulin) hours. Samples were collected in vacuum blood collection tubes containing disodium EDTA and immediately placed on ice. The samples were centrifuged, and the resulting plasma was transferred to polypropylene test tubes and stored on ice or refrigerated for the duration of the study.

At the conclusion of the experiment, the animal was anesthetized (isoflurane); the catheter was flushed with fresh saline and filled with the glycerol/heparin mixture; the free end of the catheter was knotted and placed subcutaneously as described earlier; and antibiotic was administered (300 mg Keflex, I.M.). Plasma glucose concentrations were determined the day of the study using a glucose oxidase method in a Beckman glucose analyzer. Values are listed as the mean ± the standard error of the mean (SEM).

The plasma glucose concentration did not change significantly from baseline during the two-hour observation period following injection of phosphate buffered saline (Table 1). Over the same period of time, subcutaneous administration of B28-N$^{\epsilon}$-Palmitoyl Lys$^{B28}$Pro$^{B29}$-human insulin resulted in a 15% (17 mg/dl) decrease in the plasma glucose concentration. The plasma glucose concentration in the B28-N$^{\epsilon}$-Palmitoyl Lys$^{B28}$Pro$^{B29}$-human insulin-treated animal continued to fall gradually over the next four hours, falling to a glucose level mg/dl below baseline (35% decrease) six hours post-injection. It is established in the literature that plasma glucose concentrations in the normal dog do not fall significantly even after a week of fasting. The decrease in glucose observed in this study was due to the administration of B28-N$^{\epsilon}$-Palmitoyl Lys$^{B28}$Pro$^{B29}$-human insulin, thus demonstrating the insulin-like activity of this compound.

TABLE 1

Plasma glucose concentrations following subcutaneous injection of phosphate-buffered saline (controls) or B28-N$^{\epsilon}$-Palmitoyl Lys$^{B28}$Pro$^{B29}$-human insulin.

| Time (minutes) | Control (n = 5) (mg/dL) | B28-N$^{\epsilon}$-Palmitoyl Lys$^{B28}$Pro$^{B29}$-human insulin (n = 1) (mg/dL) |
| --- | --- | --- |
| −15 | 114 ± 3 | 116 |
| 0 | 112 ± 3 | 116 |
| 30 | 117 ± 4 | 114 |
| 60 | 114 ± 3 | 107 |
| 90 | 115 ± 3 | 102 |
| 120 | 117 ± 5 | 99 |
| 150 |  | 101 |
| 180 |  | 100 |
| 210 |  | 100 |
| 240 |  | 98 |
| 270 |  | 87 |
| 300 |  | 82 |
| 330 |  | 79 |
| 360 |  | 75 |

We claim:

1. A mono-acylated insulin analog of the formula: SEQ ID NO:1 properly cross-linked to SEQ ID NO:2, or a pharmaceutically acceptable salt thereof, wherein Xaa at position 1 of SEQ ID NO:1 is Gly or acylated Gly when Xaa at position 1 of SEQ ID NO:2 is Phe, Xaa at position 28 of SEQ ID NO:2 is Asp, Lys, Leu, Val, or Ala, and Xaa at position 29 of SEQ ID NO:2 is Pro;

Xaa at position 1 of SEQ ID NO:2 is Phe or acylated Phe when Xaa at position 1 of SEQ ID NO:1 is Gly, Xaa at position 28 of SEQ ID NO:2 is Asp, Lys, Leu, Val, or Ala, and Xaa at position 29 of SEQ ID NO:2 is Pro;

Xaa at position 28 of SEQ ID NO:2 is Asp, Lys, Leu, Val, or Ala or acylated Lys when Xaa at position 1 of SEQ ID NO:1 is Gly, Xaa at position 1 of SEQ ID NO:2 is Phe, and Xaa at position 29 of SEQ ID NO:2 is Pro; and Xaa at position 29 of SEQ ID NO:2 is Pro.

2. The mono-acylated insulin analog of claim 1 wherein Xaa at position 1 of SEQ ID NO:1 is Gly.

3. The mono-acylated insulin analog of claim 2 wherein Xaa at position 1 of SEQ ID NO:2 is Phe.

4. The mono-acylated insulin analog of claim 3, wherein Xaa at position 28 of SEQ ID NO:2 is acylated Lys.

5. A mono-acylated insulin analog of claim 1 wherein the acylating group is a $C_{13}-C_{17}$ fatty acid.

6. A mono-acylated insulin analog of claim 2 wherein the acylating group is a $C_{13}-C_{17}$ fatty acid.

7. A mono-acylated insulin analog of claim 3 wherein the acylating group is a $C_{13}-C_{17}$ fatty acid.

8. A mono-acylated insulin analog of claim 4 wherein acylated Lys is a Lysine acylated with a $C_{13}-C_{17}$ fatty acid.

9. B28-$N^\epsilon$-palmitoyl-Lys$^{B28}$Pro$^{B29}$-human insulin.

10. A parenteral pharmaceutical formulation, which comprises a mono-acylated insulin analog of claim 1 together with one or more pharmaceutically acceptable preservatives, isotonicity agents, or buffers.

11. A parenteral pharmaceutical formulation, which comprises a mono-acylated insulin analog of claim 2 together with one or more pharmaceutically acceptable preservatives, isotonicity agents, or buffers.

12. A parenteral pharmaceutical formulation, which comprises a mono-acylated insulin analog of claim 3 together with one or more pharmaceutically acceptable preservatives, isotonicity agents, or buffers.

13. A parenteral pharmaceutical formulation, which comprises a mono-acylated insulin analog of claim 4 together with one or more pharmaceutically acceptable preservatives, isotonicity agents, or buffers.

14. A parenteral pharmaceutical formulation, which comprises a mixture of insulin or insulin analog and a mono-acylated insulin analog of claim 1, wherein the ratio by weight of the two components is about 1–99:99–1.

15. A parenteral pharmaceutical formulation of claim 14 wherein the mixture is Lys$^{B28}$Pro$^{B29}$-human insulin and B28-$N^\epsilon$-palmitoyl-Lys$^{B28}$Pro$^{B29}$-human insulin.

16. A method of treating a patient suffering from hyperglycemia, which comprises administering to said patient a pharmaceutical composition containing an effective amount of the mono-acylated insulin analog of claim 1.

17. A method of treating a patient suffering from hyperglycemia, which comprises administering to said patient a pharmaceutical composition containing an effective amount of the mono-acylated insulin analog of claim 2.

18. A method of treating a patient suffering from hyperglycemia, which comprises administering to said patient a pharmaceutical composition containing an effective amount of the mono-acylated insulin analog of claim 3.

19. A method of treating a patient suffering from hyperglycemia, which comprises administering to said patient a pharmaceutical composition containing an effective amount of the mono-acylated insulin analog of claim 4.

20. B28-$N^\epsilon$-myristoyl-Lys$^{B28}$Pro$^{B29}$-human insulin.

21. B1-$N^\alpha$-palmitoyl-Lys$^{B28}$Pro$^{B29}$-human insulin.

22. B1-$N^\alpha$-myristoyl-Lys$^{B28}$Pro$^{B29}$-human insulin.

23. A parenteral formulation, which comprises the mono-acylated insulin analog of claim 9 together with one or more pharmaceutically acceptable preservatives, isotonicity agents, or buffers.

24. A parenteral formulation, which comprises the mono-acylated insulin analog of claim 20 together with one or more pharmaceutically acceptable preservatives, isotonicity agents, or buffers.

25. A parenteral formulation, which comprises the mono-acylated insulin analog of claim 21 together with one or more pharmaceutically acceptable preservatives, isotonicity agents, or buffers.

26. A parenteral formulation, which comprises the mono-acylated insulin analog of claim 22 together with one or more pharmaceutically acceptable preservatives, isotonicity agents, or buffers.

27. The parenteral pharmaceutical formulation of claim 14 wherein the mixture is Lys$^{B28}$Pro$^{B29}$-human insulin and B28-$N^\epsilon$-myristoyl-Lys$^{B28}$Pro$^{B29}$-human insulin.

28. The parenteral pharmaceutical formulation of claim 14 wherein the mixture is Lys$^{B28}$Pro$^{B29}$-human insulin and B1-$N^\alpha$-palmitoyl-Lys$^{B28}$Pro$^{B29}$-human insulin.

29. The parenteral pharmaceutical formulation of claim 14 wherein the mixture is Lys$^{B28}$Pro$^{B29}$-human insulin and B1-$N^\alpha$-myristoyl-Lys$^{B28}$B$^{29}$Pro-human insulin.

30. A method of treating a patient suffering from hyperglycemia, which comprises administering to said patient a pharmaceutical composition containing an effective amount of the mono-acylated insulin analog of claim 9.

31. A method of treating a patient suffering from hyperglycemia, which comprises administering to said patient a pharmaceutical composition containing an effective amount of the mono-acylated insulin analog of claim 20.

32. A method of treating a patient suffering from hyperglycemia, which comprises administering to said patient a pharmaceutical composition containing an effective amount of the mono-acylated insulin analog of claim 21.

33. A method of treating a patient suffering from hyperglycemia, which comprises administering to said patient a pharmaceutical composition containing an effective amount of the mono-acylated insulin analog of claim 22.

\* \* \* \* \*